(12) United States Patent
Hong et al.

(10) Patent No.: US 10,139,331 B2
(45) Date of Patent: Nov. 27, 2018

(54) FILTRATION MEMBRANE FOULING INDEX MEASURING METHOD

(71) Applicant: DOOSAN HEAVY INDUSTRIES & CONSTRUCTION CO., LTD., Changwon-si, Gyeongsangnam-do (KR)

(72) Inventors: Seung Kwan Hong, Yongin-si (KR); Young Gil Ju, Yuseong-gu (KR); Jung Won Kim, Seoul (KR); Yong Xun Jin, Seoul (KR)

(73) Assignee: DOOSAN HEAVY INDUSTRIES & CONSTRUCTION CO., LTD., Changwon-Si (KR)

( * ) Notice: Subject to any disclaimer, the term of this patent is extended or adjusted under 35 U.S.C. 154(b) by 401 days.

(21) Appl. No.: 14/651,304

(22) PCT Filed: Dec. 5, 2013

(86) PCT No.: PCT/KR2013/011231
§ 371 (c)(1),
(2) Date: Jun. 11, 2015

(87) PCT Pub. No.: WO2014/092383
PCT Pub. Date: Jun. 19, 2014

(65) Prior Publication Data
US 2015/0323442 A1 Nov. 12, 2015

(30) Foreign Application Priority Data

Dec. 12, 2012 (KR) .......... 10-2012-0144491

(51) Int. Cl.
*G01N 15/08* (2006.01)
*B01D 61/12* (2006.01)
*B01D 65/10* (2006.01)

(52) U.S. Cl.
CPC .......... *G01N 15/0826* (2013.01); *B01D 61/12* (2013.01); *B01D 65/10* (2013.01); *G01N 2015/086* (2013.01)

(58) Field of Classification Search
CPC .... B01D 61/12; B01D 65/10; G01N 15/0826; G01N 2015/086
(Continued)

(56) References Cited

U.S. PATENT DOCUMENTS 9,579,607 B2 * 2/2017 Hong .................... B01D 65/10

FOREIGN PATENT DOCUMENTS

| JP | 10-286445 A | 10/1998 |
| JP | 2003-251153 A | 9/2003 |

(Continued)

OTHER PUBLICATIONS

Youngbeom Yu "Evaluation of membrane fouling potential by multiple membrane array system (MMAS): Measurements and applications" (Jul. 2010), pp. 279-288, vol. 362, issues 1-2, *Journal of Membrane Science*, Republic of Korea.
(Continued)

*Primary Examiner* — John H Le
(74) *Attorney, Agent, or Firm* — Sughrue Mion, PLLC

(57) ABSTRACT

A filtration membrane fouling index measuring method including: (a) serially connecting two filtration membranes having the same membrane properties, and sequentially passing influent water therethrough; (b) measuring the flow volume that has passed through the first of the filtration membranes; (c) measuring the flow volume that has passed through the second of the filtration membranes; (d) measuring the cumulative pass-through volume that has passed through the first or the second filtration membrane; and (e) determining the fouling index of the filtration membrane, based on the flow volume that has passed through the first
(Continued)

filtration membrane, the flow volume that has passed through the second filtration membrane and the cumulative pass-through volume. The method eliminates pore-blocking-induced measurement errors that occur with measurement methods involving Modified Fouling Index which is a fouling index for filtration membranes.

9 Claims, 6 Drawing Sheets

(58) Field of Classification Search
USPC ........... 702/34, 50, 55; 73/38; 210/104, 106, 210/636, 639, 652, 654
See application file for complete search history.

(56) References Cited

FOREIGN PATENT DOCUMENTS

| | | | |
|---|---|---|---|
| KR | 10-2010-0057262 A | 5/2010 | |
| KR | 10-2011-0067744 A | 6/2011 | |
| KR | 10-1181549 B1 | 9/2012 | |

OTHER PUBLICATIONS

Samer Adham et al "Final Report: Crossflow Sampler Fouling Index" Montgomery Watson Harza (MWH), Pasadena, CA (Sep. 2007), pp. 1-28.
International Search Report of PCT/KR2013/011231 dated Feb. 26, 2014.

* cited by examiner ated on Dec. 5, 2013, which claims priority from Korean Application No. KR 10-2012-0144491, filed on Dec. 12, 2012, the contents of which are incorporated herein in their entirety.

FILTRATION MEMBRANE FOULING INDEX MEASURING METHOD

CROSS REFERENCE TO RELATED APPLICATION(S)

This application is a National Stage application of PCT International Application No. PCT/KR2013/011231, filed on Dec. 5, 2013, which claims priority from Korean Application No. KR 10-2012-0144491, filed on Dec. 12, 2012, the contents of which are incorporated herein in their entirety.

BACKGROUND

Technical Field

The present invention relates to a filtration membrane fouling index measuring method.

A reverse osmosis system or a nanofiltration process is one of technologies which have been recently noticed in various water treatment fields. Particularly, processes using the reverse osmosis system are now coming into widespread use in the field of seawater desalination or sewage recycling.

According to GWI (Global Water Intelligence) "Water Reuse Markets 2005-2015: A Global Assessment & Forecast", the global water reuse market is expected to grow from 2 million tons per day today to 5.4 million tons per day in 2015. In addition, the global seawater desalination market is expected to grow from 3 million tons per day today to 6.2 million tons per day in 2015. Besides, the reverse osmosis system or the nanofiltration process is an advanced water treatment method noticed in the field of surface water and ground water treatment, industrial wastewater treatment, and zero-discharge recycling.

However, filtration membrane fouling, namely, membrane fouling is an obstacle to the commercialization or the field installation and operation of the reverse osmosis system or the nanofiltration process. The membrane fouling refers to a phenomenon in which various foreign substances present in water flowing into a filtration membrane are deposited or adsorbed on a surface of the filtration membrane to thereby deteriorate water permeability of the filtration membrane.

There are various types of foreign substances causing the membrane fouling including suspended particles, colloids, organic matters, microbes, and mineral salts such as calcium salts. It is very difficult to predict the membrane fouling phenomenon because of these various foreign substances causing the membrane fouling.

In general, an SDI (Silt Density Index) measuring method is used to predict membrane fouling occurring in a reverse osmosis filtration membrane or a nanofiltration membrane. In the SDI measuring method, the SDI is an index indicative of a possibility in which fouling may occur in a membrane. The SDI measuring method is a method of measuring a degree of fouling caused by suspended solids (SS) when influent passes through a filter having a diameter of 47 mm and a pore size of 0.45 μm at a pressure of 30 psi.

In the SDI measuring method, an initial time $T_0$ for which 500 ml of water passes through the filter is measured, and then a time $T_1$ for which 500 ml of water passes through the filter is measured again after 15 minutes. In this case, the ratio of $T_0$ to $T_1$ is used as a measure of membrane fouling.

The SDI measuring method is currently the most widely used method to predict a propensity for membrane fouling by influent in reverse osmosis systems or nanofiltration processes. In general, severe fouling is determined to be not generated when a value measured by the SDI measuring method, namely, the measured SDI value is less than 3, whereas severe fouling is determined to be generated when the measured SDI value is equal to or greater than 5.

Alternatively, an MFI (Modified Fouling Index) measuring method is used to measure membrane fouling occurring in a reverse osmosis filtration membrane or a nanofiltration membrane. In the MFI measuring method, the MFI is a fouling index indicative of a degree of membrane fouling caused by fouling sources when influent passes through a filtration membrane having a diameter of 47 mm and a pore size of 0.45 μm at a pressure of 30 psi.

FIGS. 1 to 4 are views illustrating a membrane fouling mechanism in a filtration membrane having pores. Specifically, FIG. 1 is a view illustrating a complete blocking state, FIG. 2 is a view illustrating an intermediate blocking state, FIG. 3 is a view illustrating a standard blocking state, and FIG. 4 is a view illustrating a cake layer shape.

Here, since the membrane fouling mechanism in a reverse osmosis filtration membrane and a nanofiltration membrane corresponds to cake filtration, an MFI measuring method measures a value reflecting cake resistance as a fouling index. Therefore, the effect of pore blocking other than the cake filtration is preferably excluded to measure an MFI.

The MFI is measured using the following Equation 1.

$$\frac{t}{V} = \frac{\mu R_m}{\Delta PA} + \frac{\mu \alpha C}{2\Delta PA^2} V \qquad \text{[Equation 1]}$$

In Equation 1, V is a cumulative permeation rate, t is a time, μ is a viscosity coefficient, ΔP is a pressure difference between filtration membranes, A is an area of a filtration membrane, C is concentration of a fouling source, α is cake resistance, and $R_m$ is self-resistance of a filtration membrane.

Here, the MFI is measured using a gradient between cumulative permeation rates on the right and left hand sides of Equation 1. That is, the MFI is measured by measuring the time and cumulative permeation rate on the left-hand side of Equation 1 and by calculating the gradient, $$\frac{\mu \alpha C}{2\Delta PA^2},$$

forming a mathematical relationship with the cumulative permeation rate on the right-hand side of Equation 1.

FIG. 5 is a graph illustrating a relationship between t/V and V measured through the MFI method. In the graph of FIG. 5 illustrating the result measured through the MFI method, membrane fouling steps are divided into a pore blocking section A, a cake filtration section B, and a cake compression section C. Here, the gradient in the cake filtration section B is calculated as a MFI value.

However, the MFI is not accurately reflected by the gradient in the cake filtration section B which is actually influenced by pore blocking since the gradient in the cake filtration section B is calculated as the MFI value on the assumption that the effect of the pore blocking is excluded from measured values in the cake filtration section B illustrated in FIG. 5 in the conventional MFI method.

In addition, since the whole gradient in the cake filtration section B seems to be linear but is irregular for each segment in the cake filtration section B, the MFI value is varied according to segments selected by an operator.

SUMMARY

Accordingly, the present invention has been made in view of the above-mentioned problems, and an object thereof is to provide a filtration membrane fouling index measuring method capable of eliminating measurement errors caused by pore blocking involved in a method of measuring an MFI (Modified Fouling Index) or SDI (Silt Density Index) which is a filtration membrane fouling index.

Technical Solution

In accordance with an aspect of the present invention, the above and other objects can be accomplished by the provision of a filtration membrane fouling index measuring method including (a) connecting two filtration membranes having the same membrane properties in series so as to sequentially pass influent therethrough, (b) measuring a flow rate passing through a first filtration membrane of the filtration membranes, (c) measuring a flow rate passing through a second filtration membrane of the filtration membranes, (d) measuring a cumulative permeation rate passing through the first or second filtration membrane, and (e) measuring a fouling index of each filtration membrane, based on the flow rate passing through the first filtration membrane, the flow rate passing through the second filtration membrane, and the cumulative permeation rate.

The fouling index may reflect cake resistance from which an effect by pore blocking of the filtration membrane is excluded.

The fouling index may be measured based on $\beta/2$ in the following Equation:

$$\frac{\left(\frac{1}{Q_I} - \frac{1}{Q_P}\right)}{2} = \frac{\beta}{2} V,$$

where $Q_I$ is the flow rate passing through the first filtration membrane, $Q_P$ is the flow rate passing through the second filtration membrane, V is the cumulative permeation rate, and $\beta$ is a cake fouling index reflecting the cake resistance.

The fouling index may be measured based on $\beta/2$ in the following Equation:

$$\frac{\left(\frac{1}{Q_I} - \frac{1}{Q_P}\right)}{2} = \frac{\beta}{2} V,$$

where $Q_{OI} = Q_I - Q_O$, $Q_{OP} = Q_P - Q_O$, $Q_I$ is the flow rate passing through the first filtration membrane, $Q_P$ is the flow rate passing through the second filtration membrane, $Q_O$ is a premeasured flow rate when distilled water passes through a filtration membrane having the same membrane properties as those of the filtration membrane, V is the cumulative permeation rate, and $\beta$ is a cake fouling index reflecting the cake resistance.

The fouling index in the above (e) may be measured by calculating a gradient between a measurement value measured until the flow rates in the above (b) and (c) become a preset cumulative permeation rate to be substituted into the left-hand side of the Equation, and the cumulative permeation rate measured in the above (d).

In addition, in the above (e), $\beta/2$ values on the Equation may be calculated as a unit of a preset cumulative permeation rate, and an average of the calculated $\beta/2$ values may be measured as the fouling index.

In accordance with another aspect of the present invention, the above and other objects can be accomplished by the provision of a filtration membrane fouling index measuring method including (a) connecting two filtration membranes having the same membrane properties in series so as to sequentially pass influent therethrough, (b) measuring a flow rate passing through a first filtration membrane of the filtration membranes, (c) measuring a flow rate passing through a second filtration membrane of the filtration membranes, (d) calculating a reference flow rate, based on the flow rate passing through the first filtration membrane, the flow rate passing through the second filtration membrane, and a premeasured flow rate when distilled water passes through a filtration membrane having the same membrane properties as those of each filtration membrane, and (e) measuring a fouling index of the filtration membrane, based on the reference flow rate.

The fouling index may reflect cake resistance from which an effect by pore blocking of the filtration membrane is excluded.

The fouling index may be calculated by the following Equation:

$$C-SDI = \frac{\left(1 - \frac{t_i}{t_f}\right) \times 100}{T},$$

where C-SDI is the fouling index, $t_i$ is an initial time for which influent having a reference permeation rate passes through the filtration membrane, and $t_f$ is a time for which the influent having the reference permeation rate passes through the filtration membrane again after the elapse of a reference time T from the initial time.

The reference flow rate applied for measurement of the reference permeation rate may be calculated by the following Equation:

$$\frac{1}{Q_C} = \frac{1}{Q_I} + \frac{1}{Q_O} - \frac{1}{Q_P},$$

where $Q_C$ is the reference flow rate, $Q_I$ is the flow rate passing through the first filtration membrane, $Q_P$ is the flow rate passing through the second filtration membrane, and $Q_O$ is the premeasured flow rate for the distilled water.

Advantageous Effects

In accordance with the present invention, a fouling index reflecting only cake resistance can be measured by eliminating measurement errors caused by pore blocking involved in a method of measuring an MFI (Modified Fouling Index) or SDI (Silt Density Index) which is a filtration membrane fouling index.

Additional advantages, objects, and features of the invention will be set forth in part in the description which follows and in part will become apparent to those having ordinary skill in the art upon examination of the following or may be learned from practice of the invention.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
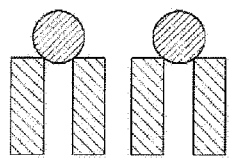
FIG. 1 is a view illustrating a membrane fouling mechanism in a filtration membrane having pores and a complete blocking state.
Figure 2:
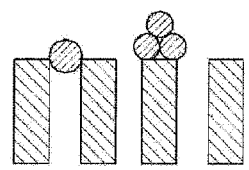
FIG. 2 is a view illustrating a membrane fouling mechanism in a filtration membrane having pores and an intermediate blocking state.
Figure 3:
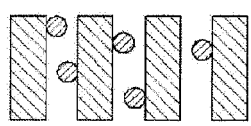
FIG. 3 is a view illustrating a membrane fouling mechanism in a filtration membrane having pores and a standard blocking state.
Figure 4:
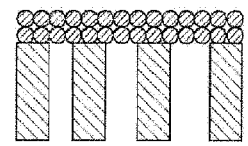
FIG. 4 is a view illustrating a membrane fouling mechanism in a filtration membrane having pores and a cake layer shape.
Figure 5:
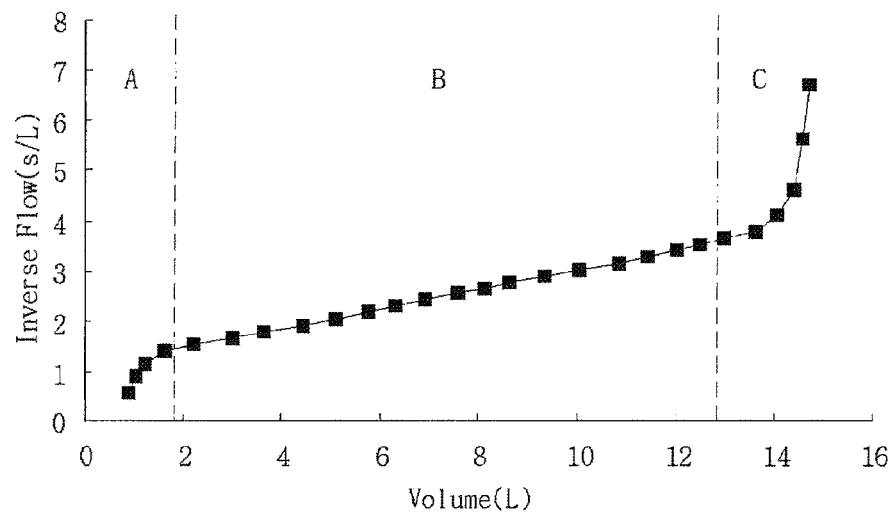
FIG. 5 is a graph illustrating a relationship between t/V and V measured through the MFI method.

Reference will now be made in detail to embodiments of the present invention, examples of which are illustrated in the accompanying drawings. Throughout the disclosure, like reference numerals refer to like parts throughout the various figures and embodiments of the present invention, and description thereof may be omitted if necessary.

First Embodiment

Figure 6:
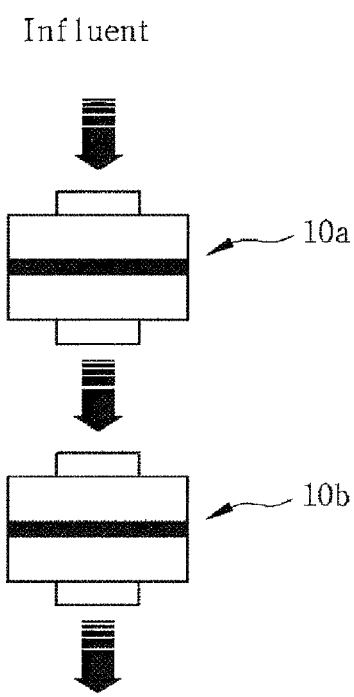
FIG. 6 is a view for explaining a principle of a filtration membrane fouling index measuring method according to a first embodiment of the present invention, two filtration membranes being connected in series in the drawing.

FIG. 6 is a view for explaining a principle of a filtration membrane fouling index measuring method according to a first embodiment of the present invention. In the filtration membrane fouling index measuring method according to the first embodiment of the present invention, two filtration membranes having the same membrane properties are connected in series so that influent sequentially passes through the series-connected filtration membranes.

For example, two filtration membranes having a pore size of 0.45 μm, which are used to measure an SDI or an MFI, are connected in series so as to measure a membrane fouling index. In this case, each of the used filtration membranes may be an MF (Microfiltration) membrane, an UF (Ultrafiltration) membrane, or a nanofiltration membrane. It is preferable that the two filtration membranes have the same membrane material, membrane area, pore size, number of pores, and the like.

Hereinafter, the filtration membrane through which influent passes first is referred to as "first filtration membrane 10a" and the filtration membrane through which influent passes second is referred to as "second filtration membrane 10b", for convenience sake of description. The fluid which passes through the first filtration membrane 10a and is then introduced into the second filtration membrane 10b is referred to as "permeate".

In a state in which the first and second filtration membranes 10a and 10b are connected in series and influent sequentially passes through the first and second filtration membranes 10a and 10b, a flow rate passing through the first filtration membrane 10a and a flow rate passing through the second filtration membrane 10b are each measured. Hereinafter, the flow rate passing through the first filtration membrane 10a is referred to as "first flow rate" and the flow rate passing through the second filtration membrane 10b is referred to as "second flow rate". Here, the measured flow rate is a permeation rate per time, for example, a flow rate having a unit of ml/min.

In addition, a cumulative permeation rate passing through the first or second filtration membrane 10a or 10b is measured. In the present invention, there is proposed an example of measuring the cumulative permeation rate of the first filtration membrane 10a on the assumption that the cumulative permeation rate of the first filtration membrane 10a is equal to the cumulative permeation rate of the second filtration membrane 10b.

In the conventional MFI method, the MFI value reflecting the cake resistance of the filtration membrane is calculated using the cumulative permeation rate as described above. However, in the present invention, a conventional MFI value, namely, a fouling index reflecting cake resistance is measured using the respective flow rates passing through the same series-connected filtration membranes and the cumulative permeation rate. Hereinafter, the fouling index reflecting cake resistance measured through the filtration membrane fouling index measuring method according to the first embodiment of the present invention is referred to as "CFI (Cake Fouling Index) value".

In more detail, the filtration membrane fouling index measuring method according to the first embodiment of the present invention calculates a CFI value using the following Equation 2.

$$\frac{\left(\frac{1}{Q_I} - \frac{1}{Q_P}\right)}{2} = \frac{\beta}{2} V \quad \text{[Equation 2]}$$

In Equation 2, $Q_I$ is a first flow rate passing through the first filtration membrane 10a, $Q_P$ is a second flow rate passing through the second filtration membrane 10a, V is a cumulative permeation rate, β is a CFI reflecting cake resistance, and β/2 is a CFI value.

The description in which the β/2 value in Equation 2 is a fouling index eliminating the effect of pore blocking from the conventional MFI method and reflecting only cake resistance will be given in detail below.

Figure 7:
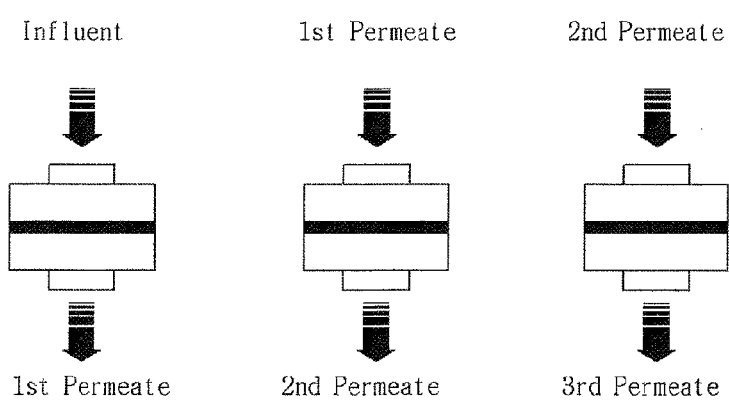
FIG. 7 is a view for explaining the principle of the filtration membrane fouling index measuring method according to the first embodiment of the present invention, three filtration membranes being connected in series in the drawing.

FIG. 7 is a view for explaining a concept in which the same three filtration membranes are connected in series and water sequentially passes therethrough.

It is widely known that standard pore blocking in the pore blocking has the greatest influence on the membrane fouling index measurement. The standard pore blocking is generated by smaller contaminants than a pore of the filtration membrane, and the contaminants are adsorbed on the membrane or are also discharged through a permeation process.

Accordingly, when an amount in contaminants causing the standard pore blocking are adsorbed on the filtration membrane and eliminated therefrom in a filtration process is not enough to affect the membrane fouling index measurement, flux declines of influent and permeate (first permeate and/or second permeate) by the standard pore blocking when they sequentially pass through the same series-connected filtration membranes will be similar to each other, as illustrated in FIG. 7.

Figure 8:
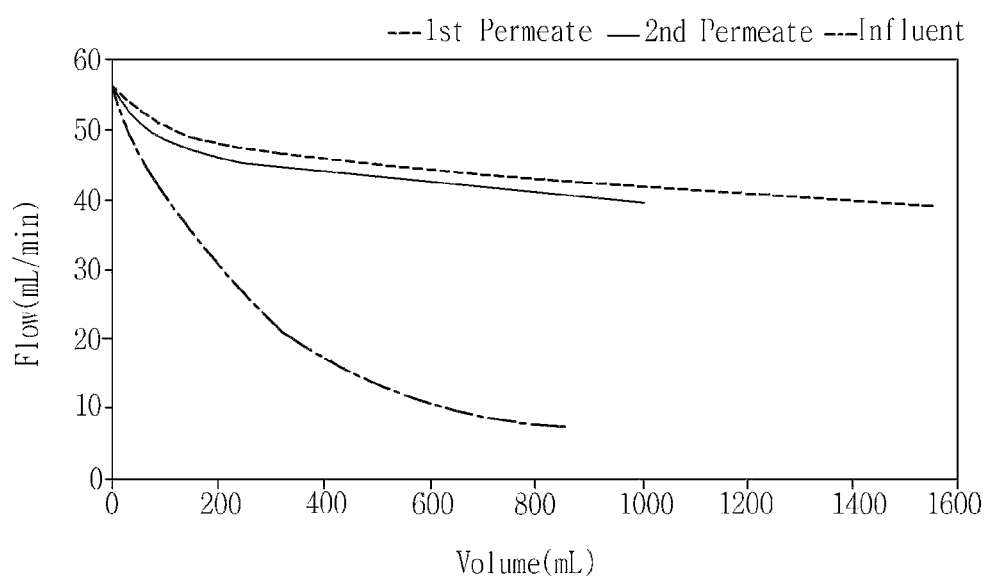
FIG. 8 is a graph illustrating a measurement result for each filtration membrane of FIG. 7.

FIG. 8 is a graph illustrating a measurement result for each filtration membrane of FIG. 7. In FIG. 8, influent mixed with a 3.5% NaCl solution and contaminants is used, and a change in flow rate of permeate (first permeate) from which a fouling source is eliminated, that is, on which cake filtration is performed while the permeate passes through the first filtration membrane and a change in flow rate of permeate (second permeate) passing through the second filtration membrane are similarly measured.

Figure 9:
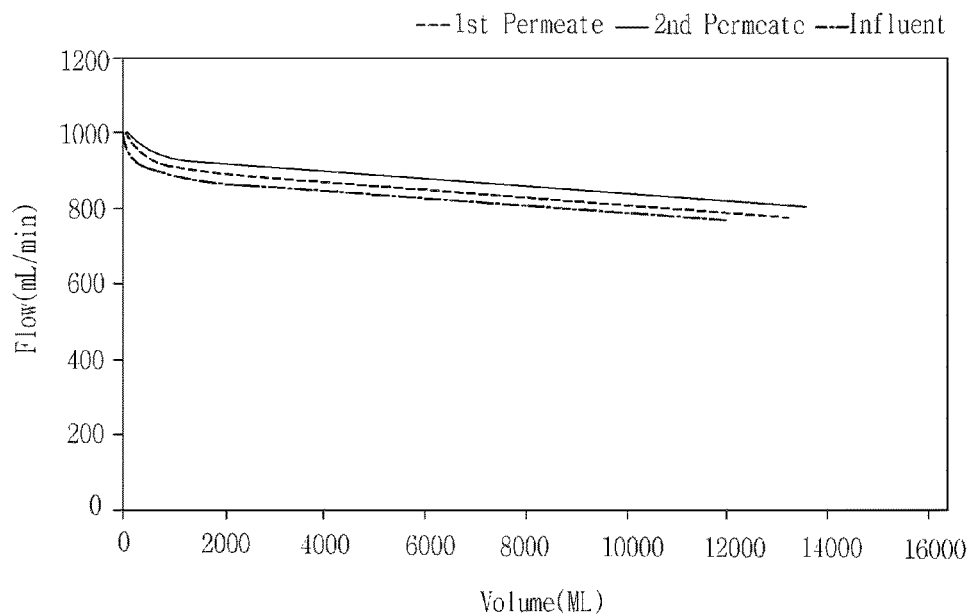
FIG. 9 is a graph illustrating a measurement result for each filtration membrane of FIG. 7, to which influent is applied differently from that of FIG. 8.

FIG. 9 is a graph illustrating another measurement result for each filtration membrane of FIG. 7. FIG. 9 illustrates a measurement result when influent containing only smaller contaminants than a pore of the filtration membrane passes through the associated filtration membrane.

As illustrated in FIGS. 8 and 9, it may be seen that the smaller contaminants than the pore of the filtration membrane have less influence on the filtration membrane after filtration. This means that the effect of the pore blocking still remains in influent or permeate (first permeate and/or second permeate).

Accordingly, as illustrated in FIG. 8, when the effect of the pore blocking is excluded from the measurement result for the influent passing through the first filtration membrane by means of the measurement result for the second filtration membrane in which the effect of the pore blocking remains, a fouling index reflecting substantial cake resistance, namely, a CFI value according to the first embodiment of the present invention may be calculated.

Hereinafter, a derivation process of Equation 2 using the above principle will be described with reference to FIG. 6.

First, fluxes of respective fluids passing through the first and second filtration membranes 10a and 10b may be indicated as the following Equation 3 and Equation 4.

$$J_I = \frac{\Delta P}{\mu(R_m + R_B + R_c)} \qquad \text{[Equation 3]}$$

$$J_P = \frac{\Delta P}{\mu(R_m + R_B)} \qquad \text{[Equation 4]}$$

In Equation 3 and Equation 4, $J_I$ is a flux in the first filtration membrane 10a, $\Delta P$ is a pressure difference between the filtration membranes, $\mu$ is a viscosity coefficient of influent, $R_m$ is self-resistance of the filtration membrane, $R_B$ is resistance by the pore blocking, $R_C$ is cake resistance, and $J_P$ is a flux in the second filtration membrane 10b. Here, since larger contaminants than the membrane pore are eliminated by the first filtration membrane 10a, $R_C$ has no influence on the second filtration membrane 10b in Equation 2.

In addition, it is assumed that the cumulative permeation rates of the fluid passing through the first and second filtration membranes 10a and 10b are equal to each other and the resistances by the pore blocking of the first and second filtration membranes 10a and 10b are equal to each other as described above in the present invention.

The following Equation 5 is derived from the above Equation 3 and Equation 4.

$$\frac{1}{J_I} - \frac{1}{J_P} = \frac{\mu(R_m + R_B + R_C)}{\Delta P} - \frac{\mu(R_m + R_B)}{\Delta P} = \frac{\mu R_C}{\Delta P} \qquad \text{[Equation 5]}$$

Here, the cake resistance $R_C$ is indicated as the following Equation 6.

$$R_C = \frac{\alpha C}{A} V \qquad \text{[Equation 6]}$$

Here, C is concentration of the fouling source, $\alpha$ is cake resistance, A is a membrane area of the filtration membrane, and V is a cumulative permeation rate as described above.

The following Equation 7 is expressed by dividing both hand sides of Equation 5 by the membrane area A of the filtration membrane and substituting the $R_C$ value into the same.

$$\frac{1}{Q_I} - \frac{1}{Q_P} = \frac{\mu \alpha C}{\Delta P A^2} V \qquad \text{[Equation 7]}$$

Equation 2 is expressed again by dividing both hand sides of Equation 7 by 2, and $\beta$ is indicated as $$\frac{\mu \alpha C}{\Delta P A^2}.$$

Equation 2 derived through the above process is in a state in which the resistance $R_B$ by the pore blocking involved in the first filtration membrane 10a is eliminated using the resistance $R_B$ by the pore blocking involved in the second filtration membrane 10b.

The $\beta/2$ value which is a CFI value is measured using Equation 2 by calculating a gradient between a measurement value measured until the first flow rate $Q_I$ passing through the first filtration membrane 10a, the second flow rate $Q_P$ passing through the second filtration membrane 10b, and the cumulative permeation rate V are a preset cumulative permeation rate to be substituted into the left-hand side of Equation 2, and the cumulative permeation rate. That is, the $\beta/2$ value is measured by calculating the gradient formed by measurement values in the graph.

Alternatively, $\beta/2$ values may be calculated by directly substituting the first flow rate $Q_I$, the second flow rate $Q_P$, and the cumulative permeation rate V, which are measured as a unit of a preset cumulative permeation rate, into Equation 2, and the average of the calculated $\beta/2$ values may be calculated as a CFI value.

Hereinafter, the effect of the filtration membrane fouling index measuring method according to the first embodiment of the present invention will be described in detail with reference to FIGS. 10 to 13. FIGS. 10 to 13 are graphs illustrating experimental results measured at a pressure of 30 psi using an MFI filtration membrane having a pore size of 0.45 μm.

Figure 10:
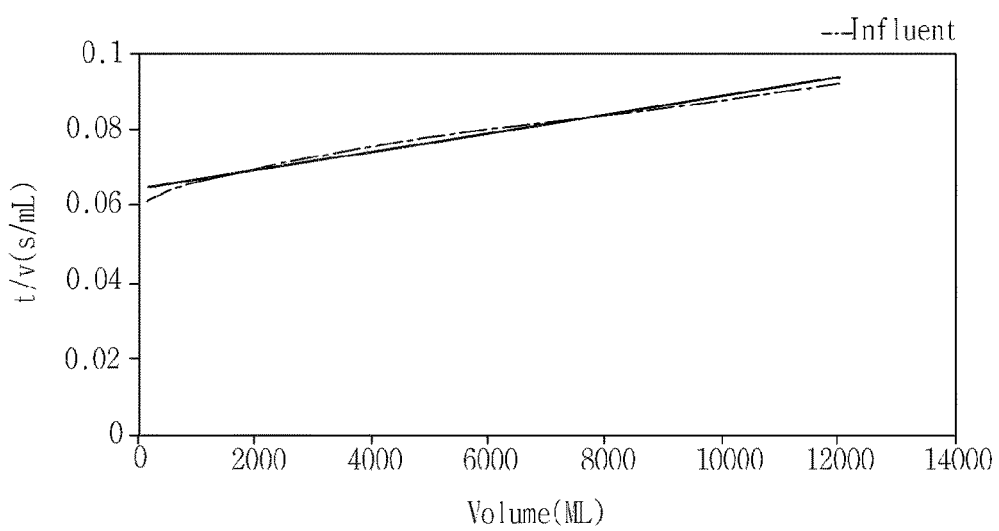
FIG. 10 is a graph illustrating a result measured through a conventional MFI (Modified Fouling Index) method.
Figure 11:
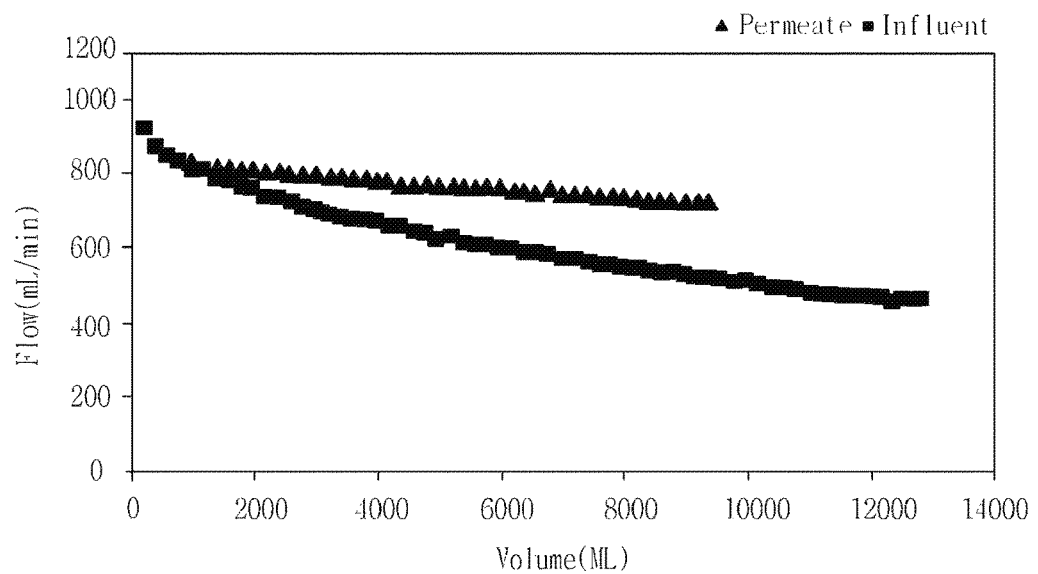
FIG. 11 is a graph illustrating a change in flow rate in the filtration membrane fouling index measuring method according to the first embodiment of the present invention.
Figure 12:
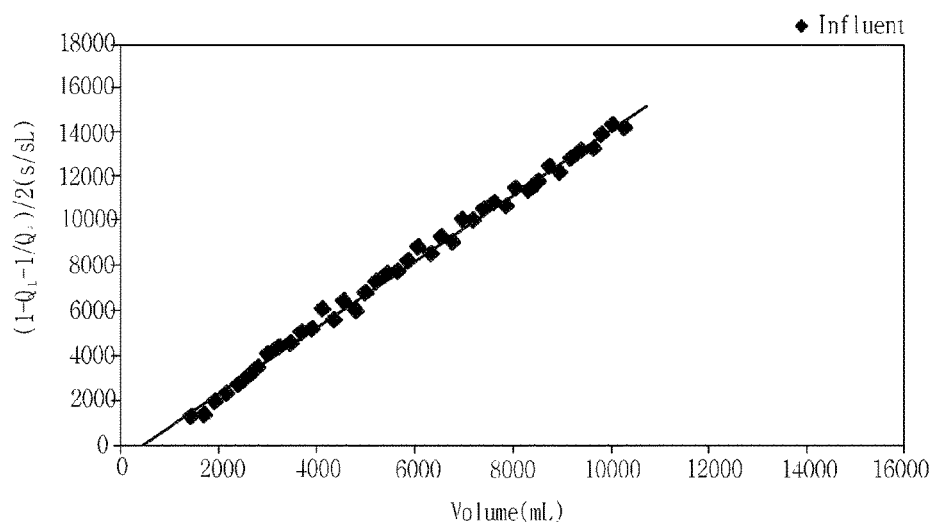
FIG. 12 is a graph for explaining an example of a fouling index calculation method in the filtration membrane fouling index measuring method according to the first embodiment of the present invention, and for using a gradient in Equation 2.
Figure 13:
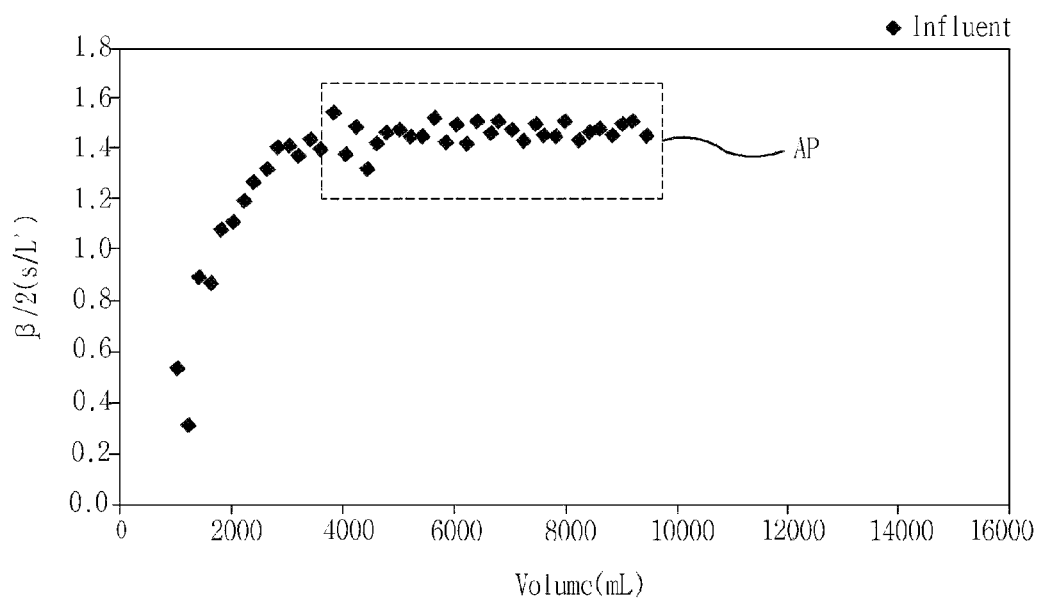
FIG. 13 is a graph for explaining another example of a fouling index calculation method in the filtration membrane fouling index measuring method according to the first embodiment of the present invention, and for directly calculating a β/2 value in Equation 2.

FIG. 10 is a graph illustrating a result measured through a conventional MFI method. FIG. 11 is a graph illustrating a change in flow rate in the filtration membrane fouling index measuring method according to the first embodiment of the present invention. FIG. 12 is a graph for using a gradient in Equation 2. FIG. 13 is a graph for directly calculating a β/2 value in Equation 2. Here, FIG. 13 illustrates an example in which the average value in an AP region is calculated as a CFI value.

The conventional MFI value is measured as 2.5 in the experimental result. However, the MFI value is measured as 1.66 by the method using the gradient and is measured as 1.55 by the method using the average in the filtration membrane fouling index measuring method according to the first embodiment of the present invention.

That is, it may be seen that the conventional MFI value is an erroneous measurement value which is greater than the actual value by the effect of the pore blocking. In other words, the conventional MFI value is measured as a greater value than that eliminating the effect of the pore blocking, thereby causing an error in which the filtration membrane is determined to be further contaminated than the actual case. For this reason, a replacement period of the filtration membrane may be unnecessarily shortened. However, according to the filtration membrane fouling index measuring method according to the first embodiment of the present invention, it may be possible to more accurately identify a replacement period of the filtration membrane.

Second Embodiment

Hereinafter, a filtration membrane fouling index measuring method according to a second embodiment of the present invention will be described. Unlike the first embodiment, the self-resistance $R_m$ of the filtration membrane varied according to a change in permeation rate is reflected in the filtration membrane fouling index measuring method of the second embodiment. That is, the self-resistance of the filtration membrane is typically varied in proportion to a time for which the filtration membrane is compressed during permeation. It is assumed that the self-resistance of the filtration membrane is not varied for conciseness of the measurement since the change in self-resistance of the filtration membrane has no great influence on the whole measurement in the first embodiment.

In more detail, similarly to the first embodiment, the fluxes in the first and second filtration membranes 10a and 10b may be indicated as the above Equation 3 and Equation 4. Here, a flux when DI water (distilled water) passes through the same filtration membrane as the first and second filtration membranes 10a and 10b may be indicated as the following Equation 8.

$$J_0 = \frac{\Delta P}{\mu R_m} \qquad [\text{Equation 8}]$$

In Equation 8, $J_O$ is a flux when the DI water passes through the filtration membrane. That is, the flux $J_O$ is influenced by the self-resistance of the filtration membrane.

The following Equation 9 and Equation 10 are derived from the above Equation 3, Equation 4, and Equation 8.

$$\frac{1}{J_I} - \frac{1}{J_O} = \frac{\mu(R_m + R_b + R_C)}{\Delta P} - \frac{\mu R_m}{\Delta P} = \frac{\mu(R_B + R_C)}{\Delta P} = \frac{1}{J_{OI}} \qquad [\text{Equation 9}]$$

$$\frac{1}{J_P} - \frac{1}{J_O} = \frac{\mu(R_m + R_B)}{\Delta P} - \frac{\mu R_m}{\Delta P} = \frac{\mu R_B}{\Delta P} = \frac{1}{J_{OP}} \qquad [\text{Equation 10}]$$

Here, the following Equation 11 is derived from the above Equation 9 and Equation 10 on the assumption that the cumulative permeation rates are equal to each other and the $R_B$ values for the first and second filtration membranes 10a and 10b are equal to each other.

$$\frac{1}{J_{OI}} - \frac{1}{J_{OP}} = \frac{\mu(R_B + R_C)}{\Delta P} - \frac{\mu R_B}{\Delta P} = \frac{\mu R_C}{\Delta P} \qquad [\text{Equation 11}]$$

The result obtained by dividing both hand sides of Equation 11 by the membrane areas A of the first and second filtration membranes 10a and 10b is indicated as the following Equation 12.

$$\frac{1}{Q_{OI}} - \frac{1}{Q_{OP}} = \frac{\mu \alpha C}{\Delta P A^2} V \qquad [\text{Equation 12}]$$

That is, the CFI value according to the second embodiment may be measured as a value on the left-hand side and a V value on the right-hand side which are measured using the gradient value $$\beta = \frac{\mu \alpha C}{\Delta P A^2}$$

by the same two methods as those described in the first embodiment. Actually, the CFI value is β/2. Here, $Q_{OI}=Q_I-Q_O$ and $Q_{OP}=Q_P-Q_O$.

Here, the $Q_O$ value for compensation of $Q_{OI}$ and $Q_{OP}$ in Equation 12, namely, the $Q_O$ value for DI water may use premeasured result values for the filtration membranes having the same properties, instead of installing separate filtration membranes having the same properties in addition to the first and second filtration membranes 10a and 10b.

Through the above method, the CFI value in which the effect of the self-resistance of the filtration membrane varied according to time is reflected may be measured.

Third Embodiment

Hereinafter, a filtration membrane fouling index measuring method according to a third embodiment of the present invention will be described. The third embodiment of the present invention is to improve a conventional SDI (Silt Density Index) measuring method.

The conventional SDI value is calculated by the following Equation 13.

[Equation 13]

$$SDI = \frac{\left(1 - \frac{t_i}{t_f}\right) \times 100}{T}$$

In Equation 13, $t_i$ is an initial time for a reference permeation rate, for example, an initial time for which 500 ml of influent passes through a filtration membrane, and $t_f$ is a time for which the influent having the reference permeation rate passes through the filtration membrane again after the elapse of a reference time T from the initial time, for example, after 15 minutes. Here, permeate typically passes through the filtration membrane at a pressure of 30 psi.

However, the SDI in the conventional SDI measuring method is measured in a state in which the effect of pore blocking is involved therein. Particularly, only fouling by cake resistance from which the effect of the pore blocking is excluded is typically detected from a reverse osmosis filtration membrane or a nanofiltration membrane, as described above.

In the filtration membrane fouling index measuring method according to the third embodiment of the present invention, a fouling index excluding the effect of the pore blocking is measured. Hereinafter, the fouling index measured through the filtration membrane fouling index measuring method according to the third embodiment of the present invention is referred to as "C-SDI".

Fluxes of respective fluids passing through the first and second filtration membranes 10$a$ and 10$b$ may be indicated as the above Equation 3 and Equation 4. A flux when DI water passes through the same filtration membrane as the first and second filtration membranes 10$a$ and 10$b$ may be indicated as the above Equation 8.

Here, when it is assumed that a filtration membrane having only self-resistance of the filtration membrane and cake resistance is present and a flux of the fluid passing through the filtration membrane is $J_C$, the flux $J_C$ may be indicated as the following Equation 14. In this case, the flux $J_C$ is in a state in which only the cake resistance is reflected therein.

$$J_C = \frac{\Delta P}{\mu(R_m + R_C)} \quad \text{[Equation 14]}$$

The following Equation 15 is derived from the above Equation 3, Equation 4, Equation 8, and Equation 14.

$$\frac{1}{J_I} - \frac{1}{J_C} + \frac{1}{J_O} = \frac{\mu(R_m + R_B + R_C)}{\Delta P} - \frac{\mu(R_m + R_C)}{\Delta P} + \frac{\mu R_m}{\Delta P} \quad \text{[Equation 15]}$$
$$= \frac{\mu(R_B + R_m)}{\Delta P} = \frac{1}{J_P}$$

The result obtained by dividing both hand sides of Equation 15 by a membrane area A is indicated as the following Equation 16.

$$\frac{1}{Q_C} = \frac{1}{Q_I} + \frac{1}{Q_O} - \frac{1}{Q_P} \quad \text{[Equation 16]}$$

When the reference flow rate $Q_C$ calculated by Equation 16 is applied as a flow rate for the reference permeation rate measured for application to Equation 13, the C-SDI value according to the present invention may be calculated. That is, the reference permeation rate applied to Equation 13 is calculated by measuring respective flow rates passing through the first and second filtration membranes 10$a$ and 10$b$ and by calculating a reference flow rate for DI water together with the premeasured flow rate.

In other words, the value calculated by Equation 13 is a C-SDI value which is a new fouling index calculated by the filtration membrane fouling index measuring method according to the third embodiment of the present invention.

Various embodiments have been described in the best mode for carrying out the invention. Although the present invention has been described with respect to the illustrative embodiments, it will be apparent to those skilled in the art that various variations and modifications may be made without departing from the spirit and scope of the invention as defined in the following claims.

The invention claimed is:

1. A filtration membrane fouling index measuring method using a first filtration membrane and a second filtration membrane, wherein the first filtration membrane and the second filtration membrane have a same membrane material, membrane area, and pore size, the method comprising:
   (a) connecting, in series, the first and second filtration membranes having the same membrane material, membrane area, and pore size;
   (b) passing fluid through the first filtration member and subsequently passing the fluid that has passed through the first filtration member through the second filtration member;
   (c) measuring a first flow rate passing through the first filtration membrane;
   (d) measuring a second flow rate passing through theft second filtration membrane;
   (e) measuring a cumulative permeation rate passing through the first or second filtration membrane; and
   (f) determining a fouling index of each of the first and second filtration membranes, based on the first flow rate passing through the first filtration membrane, the second flow rate passing through the second filtration membrane, and the cumulative permeation rate.

2. The filtration membrane fouling index measuring method according to claim 1, wherein the fouling index reflects cake resistance from which an effect by pore blocking of the first and second filtration membranes is excluded.

3. The filtration membrane fouling index measuring method according to claim 2, wherein the fouling index is determined based on $\beta/2$ in the following Equation:

$$\frac{\left(\frac{1}{Q_I} - \frac{1}{Q_P}\right)}{2} = \frac{\beta}{2} V,$$

where $Q_I$ is the first flow rate passing through the first filtration membrane, $Q_P$ is the second flow rate passing through the second filtration membrane, V is the cumulative permeation rate, and $\beta$ is a cake fouling index reflecting the cake resistance.

4. The filtration membrane fouling index measuring method according to claim 3, wherein the fouling index in the above (f) is determined by calculating a gradient between a measurement value measured until the flow rates in the above (c) and (d) become a preset cumulative permeation rate to be substituted into the left-hand side of the Equation, and the cumulative permeation rate measured in the above (e).

5. The filtration membrane fouling index measuring method according to claim 3, wherein in the above, $\beta/2$ values on the Equation are calculated as a unit of a preset cumulative permeation rate, and an average of the calculated $\beta/2$ values is measured as the fouling index.

6. The filtration membrane fouling index measuring method according to claim 2, wherein the fouling index is determined based on $\beta/2$ in the following Equation:

$$\frac{\left(\frac{1}{Q_{OI}} - \frac{1}{Q_{OP}}\right)}{2} = \frac{\beta}{2}V,$$

where $Q_{OI} = Q_I - Q_O$, $Q_{OP} = Q_P - Q_O$, $Q_I$ is the first flow rate passing through the first filtration membrane, $Q_P$ is the second flow rate passing through the second filtration membrane, $Q_O$ is a premeasured flow rate when distilled water passes through a filtration membrane having the same membrane properties as those of the filtration membrane, V is the cumulative permeation rate, and $\beta$ is a cake fouling index reflecting the cake resistance.

7. A filtration membrane fouling index measuring method using a first filtration membrane and a second filtration membrane, wherein the first filtration membrane and the second filtration membrane have a same membrane material, membrane area, and pore size, the method comprising:
  (a) connecting, in series, the first and second filtration membranes having the same membrane material, membrane area, and pore size;
  (b) passing fluid through the first filtration member and subsequently passing the fluid that has passed through the first filtration member through the second filtration member;
  (c) measuring a first flow rate passing through the first filtration membrane;
  (d) measuring a second flow rate passing through the second filtration membrane;
  (e) calculating a reference flow rate, based on the first flow rate passing through the first filtration membrane, the second flow rate passing through the second filtration membrane, and a premeasured flow rate when distilled water passes through a filtration membrane having the same membrane properties as those of each of the first and second filtration membranes; and
  (f) determining a fouling index of the filtration membrane, based on the reference flow rate.

8. The filtration membrane fouling index measuring method according to claim 7, wherein the fouling index reflects cake resistance from which an effect by pore blocking of the first and second filtration membranes is excluded.

9. The filtration membrane fouling index measuring method according to claim 8, wherein:
the fouling index is calculated by the following Equation:

$$C\text{-}SDI = \frac{\left(1 - \frac{t_i}{t_f}\right) \times 100}{T},$$

where C-SDI is the fouling index, $t_i$ is an initial time for which influent having a reference permeation rate passes through the filtration membrane, and $t_f$ is a time for which the influent having the reference permeation rate passes through the filtration membrane again after the elapse of a reference time T from the initial time; and the reference flow rate applied for measurement of the reference permeation rate is calculated by the following Equation:

$$\frac{1}{Q_C} = \frac{1}{Q_I} + \frac{1}{Q_O} - \frac{1}{Q_P},$$

where $Q_C$ is the reference flow rate, $Q_I$ is the first flow rate passing through the first filtration membrane, $Q_P$ is the second flow rate passing through the second filtration membrane, and $Q_O$ is the premeasured flow rate for the distilled water.

* * * * *